United States Patent
Ren et al.

(10) Patent No.: US 10,052,406 B2
(45) Date of Patent: Aug. 21, 2018

(54) METHOD OF MAKING WATER SOLUBLE INJECTABLE CALCIUM POLYPHOSPHATE GELS

(71) Applicant: Wayne State University, Detroit, MI (US)

(72) Inventors: Weiping Ren, Westland, MI (US); Wei Song, Warren, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 14/900,835

(22) PCT Filed: Jul. 3, 2014

(86) PCT No.: PCT/US2014/045423
§ 371 (c)(1),
(2) Date: Dec. 22, 2015

(87) PCT Pub. No.: WO2015/003140
PCT Pub. Date: Jan. 8, 2015

(65) Prior Publication Data
US 2016/0354513 A1    Dec. 8, 2016

Related U.S. Application Data

(60) Provisional application No. 61/842,737, filed on Jul. 3, 2013.

(51) Int. Cl.
*A61K 9/16* (2006.01)
*A61L 27/12* (2006.01)
(Continued)

(52) U.S. Cl.
CPC ............ *A61L 27/12* (2013.01); *A61K 9/1652* (2013.01); *A61K 9/5073* (2013.01); *A61L 27/52* (2013.01);
(Continued)

(58) Field of Classification Search
CPC ............................ A61K 9/1652; A61K 9/5073
See application file for complete search history.

(56) References Cited

U.S. PATENT DOCUMENTS

2004/0043051 A1* 3/2004 Pilliar ............... A61L 15/24
                                                              424/423
2004/0043501 A1   3/2004 Means et al.
(Continued)

OTHER PUBLICATIONS

International Search Report for PCT/US2014/045423 dated Oct. 24, 2014.
(Continued)

*Primary Examiner* — Carlos A Azpuru
(74) *Attorney, Agent, or Firm* — Brinks Gilson & Lione

(57) ABSTRACT

The present invention describes an injectable calcium polyphosphate (CPP) gel with dense structure, which can be applied as injectable bone void filler in medical field, such as orthopedic and dental applications. Amorphous CPP powder with fine particle size (<75 pm) can be completely dissolved in water, forming a homogeneous gelation phase separated from water phase. This homogeneous CPP gel with disentangled inorganic polyphosphate chains shows viscoelasticity and superior adhesion to natural bone, metal implant surfaces and other ceramic material surfaces. The CPP gel is biomimetic and biodegradable with strong osteoconductivity and osteoinductivity. The manufacturing procedure is easy and reproducible. The mechanical strength of CPP gel is controllable by modifications, such as sintering, incorporation of other biomaterials, etc.

20 Claims, 8 Drawing Sheets

(51) Int. Cl.
A61K 9/50 (2006.01)
A61L 27/52 (2006.01)
A61L 27/54 (2006.01)

(52) U.S. Cl.
CPC ........... *A61L 27/54* (2013.01); *A61L 2400/06* (2013.01); *A61L 2430/02* (2013.01); *A61L 2430/34* (2013.01)

(56) References Cited

U.S. PATENT DOCUMENTS

2007/0113951 A1* 5/2007 Huang ............... A61F 2/30756 156/89.11
2007/0178309 A1   8/2007 Omelon
2013/0039990 A1   2/2013 Xu et al.

OTHER PUBLICATIONS

Grynpas MD Pilliar RM, Kandel RA, Renlund R, Filiaggi M, Dumitriu M. "Porous calcium polyphosphate scaffolds for bone substitute applications in vivo studies." *Biomaterials* May 2002; 23(9) pp. 2063-2070.

Hench LL, West JK. "The Sol-Gel Process." *Chemical Reviews* 90(1) pp. 33-72. (1990).

Pilliar RM et al. "Porous calcium polyphosphate scaffolds for bone substitute applications — in vitro characterization." *Biomaterials* 22 pp. 963-972 (2001).

Song W, Wang Q, Wan C, Shi T, Markel D, Blaiser R, Ren W. "A novel alkali metals/strontium co-substituted calcium polyphosphate scaffolds in bone tissue engineering." *Journal of Biomedical Materials Research* vol. 98B, issue 2, pp. 255-262 (Aug. 2011).

Song W, Ren W, Wan C, Esequivel AO, Shi T, Blasier R, Markel DC. "A novel strontium-doped calcium polyphosphate/erythromycin/poly(vinyl alcohol) composite for bone tissue engineering." *J Biomed Mater Res A*.98(3), pp. 359-371 (Sep. 2011).

Dion A et al. "The effect of processing on the structural characteristics of vancomycin-loaded amorphous calcium phosphate matrices." *Biomaterials*, vol. 26, No. 21, pp. 4486-4494 (Jul. 2005).

Kasuga T. et al. "Hydrogelation of calcium metaphosphate glass." *Chemistry Letters, Chemical Society of Japan.* Aug. 2001, pp. 820-821.

Kopp, Willian, "Calcium polyphosphate coacervates: effects of thermal treatment," J Sol-Gel Sci Technol, 2011, Springer Science Business Media.

European Search Report in Application No. 14820397.9, dated Jan. 31, 2017.

* cited by examiner

US 10,052,406 B2

METHOD OF MAKING WATER SOLUBLE INJECTABLE CALCIUM POLYPHOSPHATE GELS

CROSS-REFERENCE TO RELATED APPLICATIONS

This application is a 371 national stage application of PCT/US2014/045423, filed Jul. 3, 2014, entitled "METHOD OF MAKING WATER SOLUBLE INJECTABLE CALCIUM POLYPHOSPHATE GELS," which claims priority to U.S. Provisional Patent Application Ser. No. 61/842,737, filed Jul. 3, 2013, entitled "METHOD OF MAKING WATER SOLUBLE INJECTABLE CALCIUM POLYPHOSPHATE GELS," the entire contents of which are incorporated herein by reference.

BACKGROUND

The present invention relates to the preparation of amorphous calcium polyphosphate (CPP). More specifically, the present invention relates to calcium polyphosphate in a gel form. The gel can be used in an injectable, shapable, highly viscous, bone graft scaffold for both bone and soft tissue engineering.

SUMMARY

In one embodiment, the present invention provides a method of making a material for bone or soft tissue repair of a patient. In one step, the method comprises calcining an inorganic ceramic material to produce an amorphous calcium polyphosphate composition at a calcination temperature for a calcination time. In a second step, the method comprises melting the amorphous calcium polyphosphate composition at a melting step temperature for a melting step time. In a third step, the amorphous calcium polyphosphate composition is processed to a predetermined particle size, and the particles are dissolved in an aqueous fluid for introduction to the patient.

In another embodiment, the present invention provides a method of making a composite for bone or soft tissue repair of a patient. In a first step, the method comprises producing an amorphous calcium polyphosphate composition from an inorganic ceramic material by a calcination process, wherein the calcination process has a calcination temperature of about 500 degrees Celsius and a calcination time of about 10 hours. In a second step, the amorphous calcium polyphosphate composition is melted at a melting step temperature of about 1100 degrees Celsius to about 1200 degrees Celsius for a melting step time of about 90 minutes to about 120 minutes. In a third step, the amorphous calcium polyphosphate composition is prepared into a particle size of about 1 nanometer to about 75 microns. In a fourth step, a gel-paste structure is formed in a liquid comprising at least one of distilled water, buffer, and/or other water solutions, the method optionally comprising soaking an amount of amorphous calcium polyphosphate at a soaking temperature for a soaking time with a second substance. The second substance is selected from at least one of: another amorphous inorganic ceramic powder, a crystalline inorganic ceramic powder, a metal, and a polymer, in order to form a composite calcium polyphosphate gel. In this embodiment, the gel-paste structure has a weight ratio of water to the other component or components added for introduction by way of aqueous solution to the patient.

In another embodiment, the invention is an amorphous calcium polyphosphate gel for bone or soft tissue repair of a patient. The gel is made by a method comprising a first step of producing an amorphous calcium polyphosphate composition from an inorganic ceramic material by a calcination process, wherein the calcination process has a calcination temperature and a calcination time. In a second step, the amorphous calcium polyphosphate composition is melted at a melting step temperature for a melting step time. In a third step, the amorphous calcium polyphosphate composition is prepared to a predetermined particle size. In a fourth step, the particles are dissolved in an aqueous fluid for introduction by way of an aqueous solution to the patient.

DETAILED DESCRIPTION OF THE DRAWINGS AND THE PRESENTLY PREFERRED EMBODIMENTS

Figure 1A:
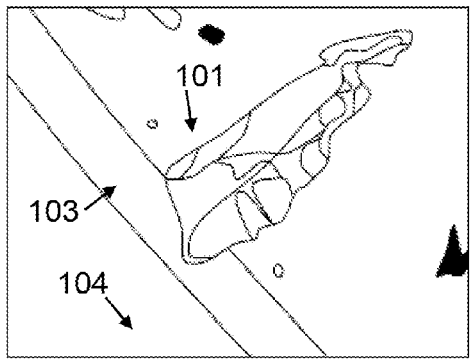
FIG. 1A-1D are views of the structures of amorphous CPP gels in accordance with one example of the present invention.

This invention is generally directed to methods for preparing an injectable inorganic ceramic gel composed of amorphous calcium polyphosphate (CPP) powder ceramics.

In one example, the method includes a defined sintering schedule to prepare amorphous CPP frits. Before sintering, different ions and minor elements can be incorporated into the amorphous frits.

This method includes preparing amorphous CPP granules or powders with controllable size (from about 10 nm to about 500 mm).

This method also includes preparation of injectable CPP gels by dissolving CPP powders of various sizes and shapes in solutions. The solutions can be sterilized water, buffered solutions with or without different salts at a variety of concentrations, different ionic strengths, and ranges of different pH values. An amorphous CPP powder with a fine particle size such that the powder is completely soluble in water represents an inventive first step in the manufacture of CPP gels to be utilized for therapeutic purposes.

As used herein, the term "about," means "approximately but not necessarily equal to," and when used in the context of a numerical value or range set forth means a variation of ±15%, or less, of the numerical value. For example, a value differing by ±15%, ±14%, ±10%, or ±5%, among others, would satisfy the definition of "about."

CPP gels can be used as a matrix for mixing different materials, including but not limited to inorganic chemicals and compounds, organic molecules, polymers, and biological molecules such as amino acids, nucleotides, nucleic acids, enzymes and other proteins, and cultured cells. The CPP gel, used alone or mixed with other materials, can be used for bone and soft tissue engineering, such as bone defect healing, medical device surface fabrication, cartilage repair, muscle repair, tendon and ligament repair and wound healing.

With the modification of various parameters, CPP gelation composites can be formulated to a desired mechanical strength and pore size range suitable for a particular application. Briefly, one method involves methods including but not limited to sintering CPP powders, grinding frits, incorporating different biomaterials by for instance soaking, and molding. Each of these steps can be modified to influence viscoelasticity, mechanical strength, porosity, pore size, and interconnectivity of the pore network. Further, if cells are included in the gel, the velocity and pattern of cell adhesion, proliferation and differentiation can be controlled by modification of the characteristics of the gel in the preceding list. For example, a CPP gel is biocompatible and can be used for biodegradable fracture fixation implants and degradable anchoring systems for temporary stabilization of bone-interfacing implants designed for fixation by bony in-growth.

CPP gel can be used in combination with other bone ceramics and with bioactive glass, or with combinations of these types of materials. Such materials include but are not limited to hydroxyapatite, tricalcium polyphosphate, calcium sulfate, calcium carbonate, calcium chloride, and so forth. The formed composites can be used as a new bone-like bone graft substitute, which is of higher viscoelasticity, higher adhesion, desired pore size, good biocompatibility, highly adjustable mechanical strength and biodegradation. These injectable bone grafts can be easily delivered to the lesion site through a regular syringe, pipet, or injection gun, which is an advantage conferred by the fact that the bone-filling gel is shapeable and flexible.

In another aspect, the invention relates to a combined use of CPP gel as a targeted and local drug and stem cell delivery tool. Molecules or cells of interest can be soaked into the gel matrix and the complex can be introduced to a site in or on a body, resulting in the delivery of the material of interest. The types of compounds which can be introduced include but are not limited to: antibiotics, such as those selected from the families of minoglycosides, ansamycins, carbapenems, cephalosporins, glycopeptides, lincosamides, lipopeptides, macrolides, penicillins, tetracyclines, and others; growth factors, such as angiopoietin(Ang), bone morphogenetic proteins (BMPs), erythropoietin (EPO), fibroblast growth factor (FGF), growth differentiation factor-9 (GDF9), insulin-like growth factor (IGF), nerve growth factor (NGF) and other neurotrophins, platelet-derived growth factor (PDGF), transforming growth factor alpha (TGF-α), transforming growth factor beta(TGF-β), vascular endothelial growth factor (VEGF), placental growth factor (PIGF), and others; and compounds of another pharmaceutical genus. Furthermore, cells can be soaked into the matrix and delivered to the site of interest. Cell types could be any type of cell or cells from humans or animals. They can be either well-differentiated cells (from commercially-available cell lines or isolated from animal or human tissues) or stem cells found in any multicellular organism that can divide (through mitosis) and differentiate into diverse specialized cell types and can self-renew to produce more stem cells. The stem cells can either be embryonic stem cells or adult stem cells, which are found in various tissues.

The invention will now be described with reference to the accompanying drawings. Although this invention has been particularly shown and described with reference to preferred embodiments thereof, it will be understood by those skilled in the art that various changes in form and details may be made therein without departing from the scope of the invention encompassed by the appended claims.

As used herein, the term "inorganic powder material" means a powder of an inorganic or ceramic material such as for example calcium polyphosphate.

The invention disclosed herein is made possible by the discovery of the mechanism acting during CPP gelation and the effects of amorphous CPP length and particle size on the physiochemical properties of a CPP gel. This discovery has resulted in the design of calcinations and grinding procedures that lead to the reliable formation of injectable CPP scaffolds.

With reference to the drawings, FIG. 1A illustrates the formation of an amorphous CPP gel 101 when amorphous CPP powder is thoroughly mixed in distilled water and the continuing phase of viscous CPP gel is separated from water. Amorphous CPP powders can be made using methods that have been described previously in detail (Filiaggi M. J. et al., Bioceramics 11:341-344, 1998; and Pilliar R. M. et al., Biomaterials 22:963-972, 2001). Amorphous CPP frits are produced by pre-calcining calcium phosphate monobasic monohydrate crystals (Ca[H2PO4]2:H2O) followed by a complete calcination for about 4 to 72 hours, or about 4 to about 16 hours, or about 8 to about 24 hours, or about 8 to about 12 hours, or about 9 to about 12 hours, or about 9 to about 11 hours, more preferably about 10 hours at a temperature of about 300° C. to about 700° C., preferably about 400° C. to about 600° C., more preferably about 475° C. to about 525° C., more preferably about 500° C. This process results in the formation of CPP following the reaction $nCa(H_2PO_4)_2:H_2O \rightarrow [Ca(PO_3)_2]_n + 3nH_2O$.

Continuing the description of the amorphous CPP gel method, the method involves forming a gel-paste structure 101 in a liquid comprising at least one of distilled water, buffer, and/or other water solutions, including soaking an amount of amorphous calcium phosphate with an amount of at least one other chemical entity such as another amorphous inorganic ceramic powder, a crystalline inorganic ceramic powder, a metal, and a polymer. The soaking temperature is preferably from about 25° C. to about 60° C. The soaking temperature may be about 25° C., or it may be about 60° C.

Bioceramics powders are well suited for this application due to the resultant biocompatible gel or ceramic. Among the sources of bioceramics powders are such materials, alone or in combination, as hydroxyapatite, octacalcium phosphate, beta-tricalciumphosphate (whitlockite), alpha-tricalcium phosphate, amorphous calcium phosphate, monocalcium phosphate monohydrate, anhydrous monocalcium phosphate, dicalciumphosphatedihydrate (brushite), anhydrous dicalcium phosphate (monetite), tetracalcium phosphate, bioglass, silica ceramics, oxide ceramics, and carbon fiber. Suitable metals include, but are not limited to, for instance one or more of magnesium, magnesium alloy, titanium, titanium alloy, cobalt-chromium alloy, and stainless steel.

Among the polymers that may be suitable for inclusion in the gel are one or more of polycarboxylates, polysulfates, polysulfonates, polyphosphates, polyamines, polyurea, polyamides, polyalkylene oxide diols, polyalhylene oxide diamines, polycarbonate, polylactone, polyethersulfone, polyvinyls, polypeptide, polysaccharide, polyurethanes, polysulfones, polycarbonates, polyesters, polyethylene, polypropylene, polystyrene, polysilicone, poly(acrylonitrile-butadienestyrene), polybutadiene, polyisoprene, polymethylmethacrylate, polyvinylacetate, polyacrylonitrile, polyvinyl cloride, polyethylene terephtalate, cellulose and other polysaccharides, polysilicones, polyolefins, polyvinyl derivatives, polypeptide derivatives, poly(lactic-co-glycolic acid), cyanoacrylate, a cyanoacrylate derivative, and polysaccharide derivatives, though this is not an exhaustive list and other polymers not listed here may be included as well.

Organic compounds may also be added to the gel. These include but are not limited to: at least one of a carboxylate, a sulfate, a sulfonate, a phosphate, an amine, urea, an amide, an alkylene oxide diol, an alhylene oxide diamine, a carbonate, a lactone, an ethersulfone, a vinyl, a peptide, a dimethacrylate, a saccharide, a urethane, a sulfone, an ester, an ethylene, propylene, a styrene, silicone, acrylonitrile-butadienestyrene, butadiene, an isoprene, methylmethacrylate, vinylacetate, acrylonitrile, vinyl cloride, ethylene terephtalate, an olefin, a vinyl derivative, bisphenol A, bisphenol A derviatives, an oligosaccharide, a peptide derivative, lactic acid, glycolic acid, cyanoacrylate, and a saccharide derivative.

The CPP is then melted at preferably about 1100° C. to about 1300° C., preferably about 1100° C., for about 10 minutes to about 360 minutes, or for about 60 to about 180 minutes, or for about 60 minutes to about 120 minutes, or from about 90 to about 120 minutes, and quenched in deionized distilled water at room temperature to produce amorphous CPP. The resulting amorphous CPP frit may be ground in a planetary ball mill, such as one sold by Fritsch Planetary Micro Mill, and subsequently screened using laboratory test mesh sieves to separate out particles that are smaller than about 1 mm in diameter, preferably using a 200 mesh sieve, preferably isolating particles about 75 µm or smaller. Prior to and in between usage, powders are stored in a vacuum desiccator.

Changing the calcining temperature and time can change the length of CPP chains. A preferred embodiment of this invention is carrying out the sintering at about 1100° C. to about 1200° C., preferably at about 1200° C. for about 90 to about 120 minutes, which results in a degree of polymerization(D.P.) of about 100. The D.P. increases with increased calcining temperature and time.

Amorphous CPP powder with particle size less than or equal to about 75 µm can be added to distilled $H_2O$ preferably at a concentration of about 0.01 to about 0.5 g/mL, more preferably about 0.05 g/mL. The mixture is then stirred or mixed in a vortex mixer (vortexed) at about 4° C. to about 90° C., or about 25° C. to about 90° C., or about 60° C., or about 25° C., for about 1 hour to about 168 hours, or about 1 hour to about 24 hours, more preferably about 1.5 to about 12 hours, more preferably about 2 hours and then cooled to about room temperature (about 25° C.) This results in formation of a slurry mixture. The slurry mixture is allowed to stand for at least about 4 hours. During this time the CPP becomes collodial, and the colloid can be manipulated to the point where it can be forced through a syringe or pipet; therefore it is injectable.

Figure 1B:
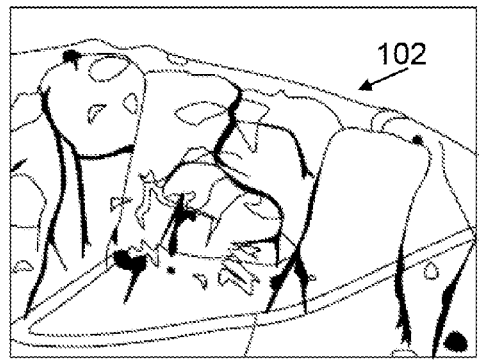

Continuing with FIG. 1A, a phase separation 103 between CPP colloid 101 and water 104 after pre-gelation can be observed. The CPP colloid 101 undergoes gelation after injection and becomes solid 102 within about 60 minutes (FIG. 1B.)

Similarly, a process for the formation of a composite CPP gel can involve mixing crystallized CPP powder with amorphous CPP gel (both consisting of particle size less than about 75 mm), in preferably a ratio of about 1:1 to about 1:10, most preferably about 1:2 ratio. This mixture of powders is added to distilled water, most preferably at a concentration of about 0.05 g of powder per milliliter of water. The mixture is stirred most preferably at about 60° C. for about 2 hours and then cooled to about room temperature. The resulting composite then undergoes an incubation period of about 2 to about 48 hours, preferably about 4 to about 16 hours, to permit colloidal formation.

A range of water content and, therefore, solid powder content can be used in order to form the CPP gel depending on the desired attributes of the final product. The water content of the mixture is preferably about 20% to about 99% of the weight of the mixture. As a result, the quantity of powder is preferably about 1% to about 80% of the weight of the mixture.

Figure 1C:
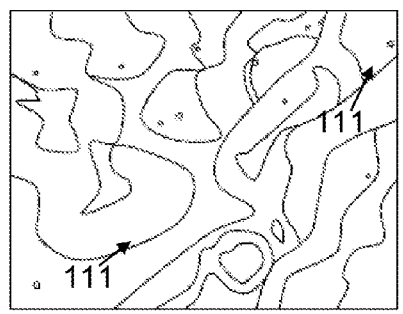

A composite CPP gel can be generally more viscous than the amorphous colloid that results from the process which utilizes only amorphous CPP as a starting material. Under the light microscope, the CPP composite gel is revealed to have a structure consisting of a continuous colloidal liquid phase integrated with a more or less even distribution of crystallized CPP granules 111 in suspension (FIG. 1C.) The CPP composite colloid is injectable, and there is a phase separation 103 between CPP composite colloid and water after pre-gelation. The CPP mix depicted in FIG. 1C depicts a CPP composite gel after gelation. Its composition, by weight ratio, is 1:0.5:10 of (amorphous CPP:crystalline CPP:water).

Figure 1D:
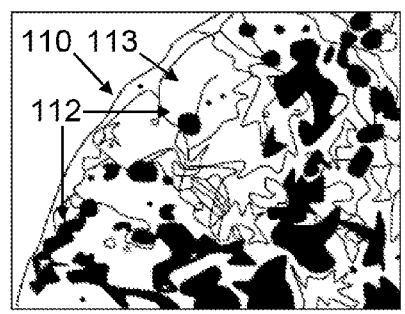

After drying the gel at room temperature for most preferably 1 hour, the distinctive two phase appearance of a bioactive glass structure 110 with crystallized CPP particles is observed under light microscopy comprising a continuous glass phase 113 evenly integrated with crystallized CPP granules 112 (FIG. 1D). The composition depicted in FIG. 1D is shown after setting. The water has evaporated, leaving a composition comprising (amorphous CPP:crystalline CPP) of 2:1 by weight.

Figure 2:
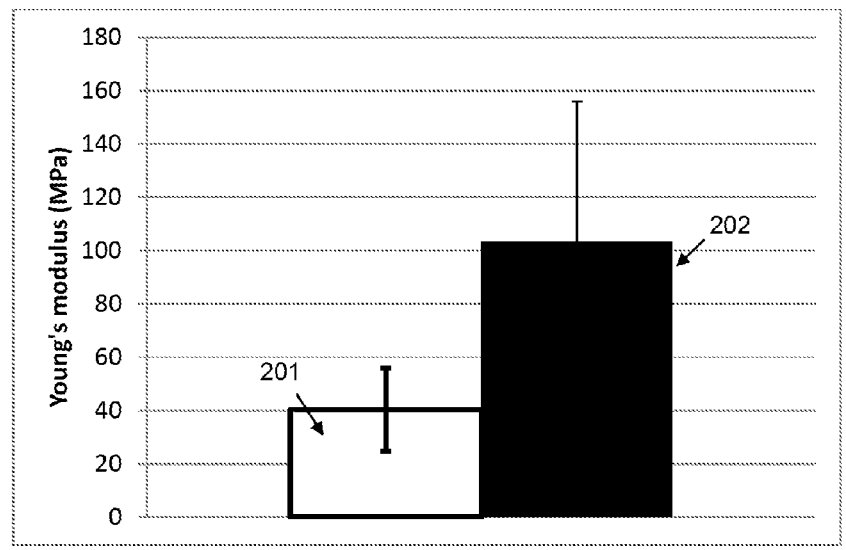
FIG. 2 is a graphical representation of results of compression tests of CPP gels in accordance with another example of the present invention.

Turning now to FIG. 2, a graphical representation of a compression test for the two types of CPP gel described above is presented. To generate this figure, pure amorphous CPP and mixed amorphous/crystalline composite suspensions were allowed to set in cylindrical casting gels measuring about 6 by about 6 mm. These samples were tested in unconfined uniaxial compression using a universal servo-hydraulic test machine (Instron 4302) at a speed of about 0.01 mm/sec. The maximum strain level was set to be about 0.5 mm/sec, at which strain level failure of the specimens was observed. The engineering compressive stress ($\sigma$)-strain ($\varepsilon$) curve was calculated from the Instron linear variable differential transformer (LVDT) and load cell measurements. Each group was measured in triplicate.

As shown in FIG. 2, the obtained Young's modulus of CPP composite gel 202 is 103.54 MPa and pure amorphous CPP gel 201 is 40.36 MPa. The elevation of the stiffness of CPP composite gel is likely due to the reinforcement of CPP microcrystal fillers. It is well established that Young's modulus of trabecular bone ranges from 2 MPa to 200 MPa, therefore both pure amorphous CPP and composite amorphous/crystalline gels show similar mechanical strength to natural trabecular bone.

For load bearing implant applications, the compressive strength of injectable bone healing material is crucial for bone regeneration. The ideal bone substitute should maintain similar mechanical strength to the surrounding bone tissue, which improves osteoinduction and osteoconduction. Thus, to design a healing material for trabecular bone with Young's modulus in this range would optimize the bone regeneration process and avoid side effects, such as stress shielding. Therefore, the pure amorphous and composite amorphous/crystalline gels of this invention are well-suited to for load bearing implant applications.

Amorphous CPP colloidal liquids form gels and have good structural integrity after casting. Gel formation indicates a potential of self-densification, which makes these materials suitable for treating orthopedic defects as bone void fillers.

Figure 3:
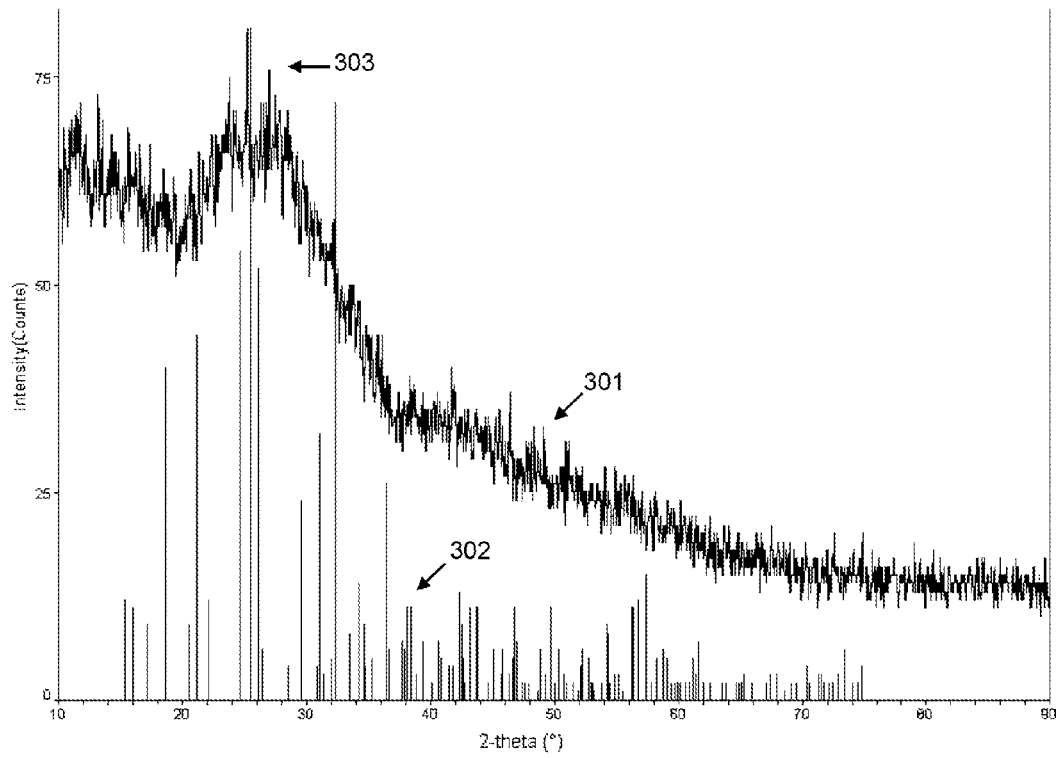
FIG. 3 is a graphical representation of powder X-ray diffraction patterns of CPP gels after solidification in accordance with another example of the present invention.

FIG. 3 shows the powder X-ray diffraction (pXRD) spectrum 301 of CPP gel after solidification. The amorphous structure was confirmed by a non-crystalline peak 303 at 20-30° and non-specific crystalline peaks. To generate this diagram, the scan speed was set to 5°/min. This data shows that when prepared as described above, amorphous CPP gel is stable in the solid phase and it is still amorphous, with no crystallization and no transition to any other crystallized Ca—P ceramics. This result reveals that the gelation of CPP colloid is distinguished from conventional calcium phosphate (ACP) cement that depends on the recrystallization from amorphous Ca—P to hydroxyapatite (HAp). The gelation of CPP colloid is followed by water evaporation and the formation of 3D network with polyphosphate chains as backbones.

Figure 4A:
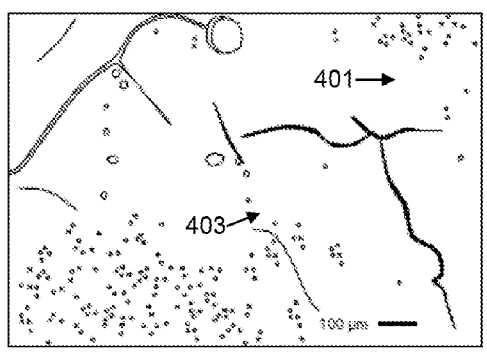
FIGS. 4A-4D are scanning electron microscope images showing the morphologies of various CPP gels in accordance with another example of the present invention.
Figure 4B:
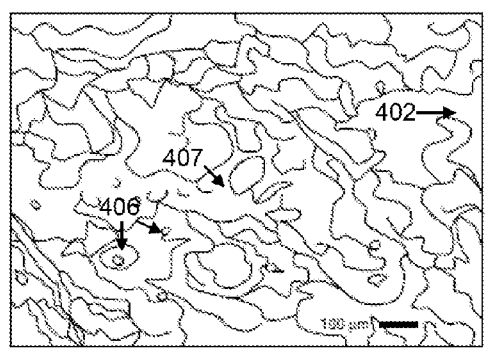
Figure 4C:
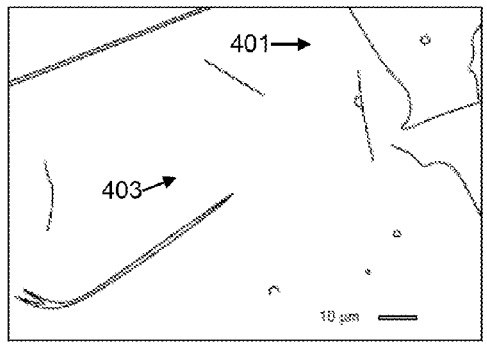
Figure 4D:
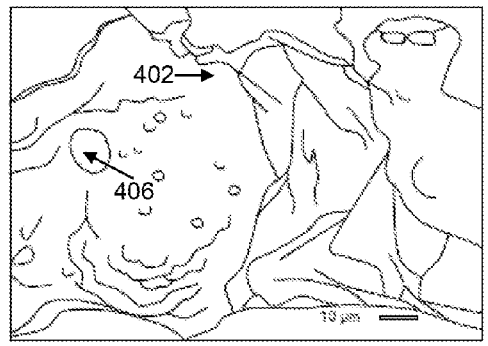

Turning now to FIG. 4A-4D, scanning electron micrographs (SEM) of the surface morphology of CPP pure amorphous 401 (FIGS. 4A and 4C,) and CPP mixed amorphous/crystalline composite 402 gels (FIGS. 4B and 4D,) after solidification. FIG. 4A/4C and show a smooth and amorphous surface 403 without obvious porous structures. The pure amorphous CPP gel has a homogenous structure.

In contrast, the CPP composite gel after gelation possesses a porous structure 404. CPP crystalline granules 406 can be observed in FIG. 4B/4D. The shrinkage limitation of crystalline CPP particles in suspension and the shrinkage capability of amorphous CPP gel in a continuous phase enable the formation of micro-scale pores 407 during gelation. The rough surface and emerged crystalline particles are readily visualized. This evidence suggests a mechanism for introducing a porous structure to the composite CPP gel. The porous structure of CPP gel can be tuned by adjusting for example the CPP crystal size used, the ratio of amorphous to crystalline powder employed, the geometry of the crystals, and other factors. The size, shape, and network structure of the pores may contribute to the gel's ability to take up, store, and release molecules, cells, or both intended for delivery to the site of injection.

Turning now to FIGS. 5-8, various rheological studies of pure amorphous and composite amorphous/crystalline CPP gels are illustrated.

Figure 5:
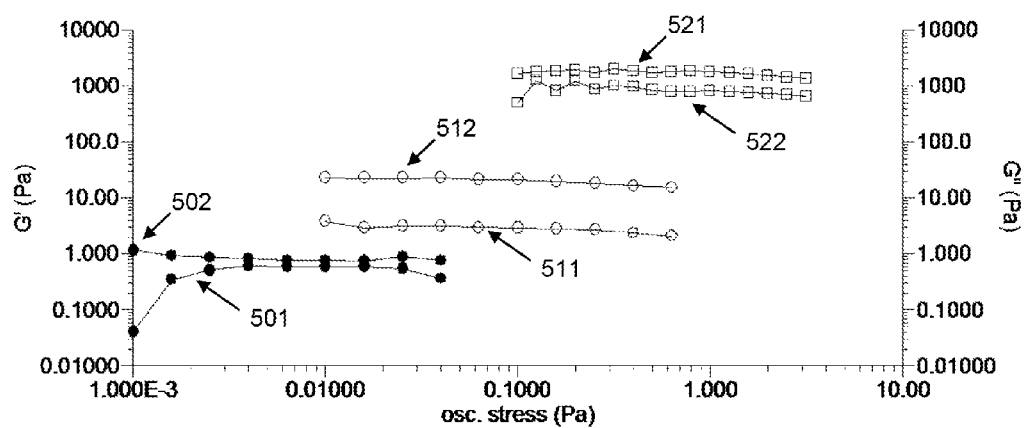
FIGS. 5-8 are graphical representations of the results of rheological tests performed on CPP gel samples in accordance with another example of the present invention.

FIG. 5 shows the rheology of pure amorphous CPP (plots 501 and 502), CPP crystalline:amorphous composite in a respective ratio of 1:2 (plots 511 and 512) and CPP crystalline:amorphous composite in a respective ratio of 1:1 (plots 521 and 522) in an oscillatory stress sweep test. Storage modulus (G') profiles (plots 501, 511, and 521) and loss modulus (G") profiles (502, 512, and 522) were generated across the linear viscoelastic region (LVR), respectively, in an oscillatory range of 0.001-10 Pa at 25° C. The viscoelasticity of all CPP gel based samples indicates that polyphosphate chain entanglement can be reversed, causing chains to disentangle when subjected to a certain level of stress. The extension of LVR for CPP gel mixed with higher amount of crystalline CPP particles reveals that an elevation level of stress is required for chain disentanglement. The conversion of G' over G" of composite crystalline:amorphous CPP mixed in a 1:1 ratio indicates a transition from viscous liquid to elastic solid.

The rheology results suggest that colloidal formation and gelation of amorphous/crystalline CPP composites could occur for reasons including but not limited to: 1) strong particle-matrix interactions between molecularly-dispersed macro-crystalline particles and polyphosphate chains, which would greatly hinder the chains mobility, causing the CPP composite to behave in a solid-like manner; 2) even distribution of macro-crystalline particles carrying a charge, which would in turn attract and link adjacent polyphosphate chains, forming a 3D network structure via weak physical interactions.

Figure 6:
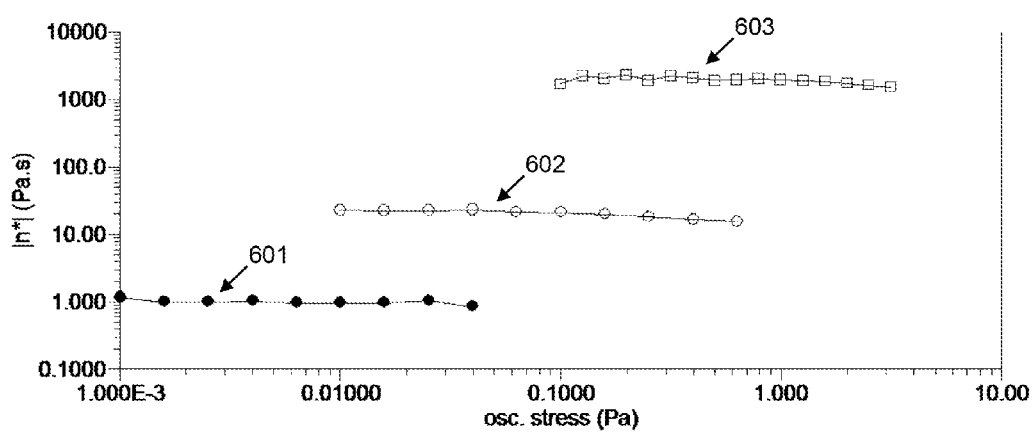

Turning now to FIG. 6, the rheological behaviors of pure amorphous CPP and composite amorphous/crystalline colloids subjected to non-destructive oscillatory stress are illustrated. These tests show that pure amorphous CPP colloid displays viscous fluid properties with a higher shear loss modulus (G") than storage modulus (G'), though both at lower levels. The complex viscosity |*η| of pure amorphous CPP colloid (plot 601) is about 1 Pa·S, which suggests comparatively lower amounts of polyphosphate chain entanglement and weak structural interactions.

Looking now at the crystalline/amorphous composites, incorporation of CPP crystalline particles increases each of G', G", and |*η| in the mixture of 1:2 ratio, with G">G', indicating that this composite is still acting as a fluid (plot 602.) Increasing the content of CPP crystalline particles to a ratio of 1:1 (plot 603) changes the properties of the composite such that G"<G', indicating that at this ratio of amorphous to crystalline CPP powder, the viscous fluid is not acting as a fluid but as a paste-like solid. The complex viscosity |*η| of CPP crystalline:amorphous 1:1 composite rose 1000-fold over that of pure amorphous CPP colloid (compare solid circles to open squares in FIG. 8.) This phenomenon indicates that the dispersed CPP crystals strongly interact with amorphous polyphosphate chains in the colloid.

The foregoing rheological studies of CPP illustrate that by changing the ratio of amorphous to crystalline CPP, the overall viscosity of CPP gels can be optimized for a wide variety of clinical applications, including but not limited to filling voids in bone, repairing cartilage, and so forth.

Figure 7:
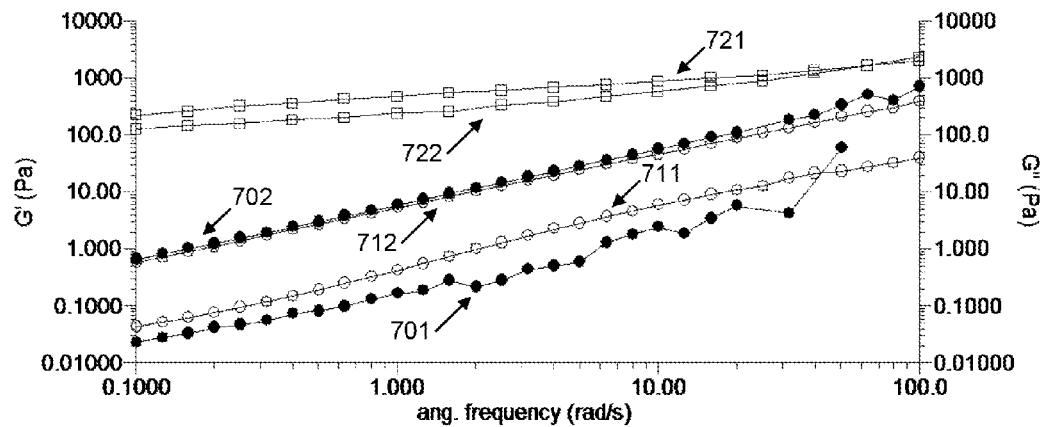

FIG. 7 shows the rheology of pure amorphous CPP (plots 701 and 702), CPP crystalline:amorphous 1:2 composite (plots 711 and 712) and CPP crystalline:amorphous 1:1 composite (plots 721 and 722) in an oscillatory frequency sweep test. Storage modulus (G', plots 701/711/721) and loss modulus (G", plots 702/712/722) profiles are shown across a frequency range of 0.1-100 rad/s at 25° C., respectively. During this relatively low frequency range, the zero-shear rate (η0) of each sample can be obtained, according to G'=η0ω, which reveals the viscosity of sample under rest and undisturbed conditions. Incorporation of CPP crystalline fillers consistently increases the η0, and the η0 of CPP crystalline:amorphous 1:1 composite is substantially higher than that of pure amorphous CPP.

Figure 8:
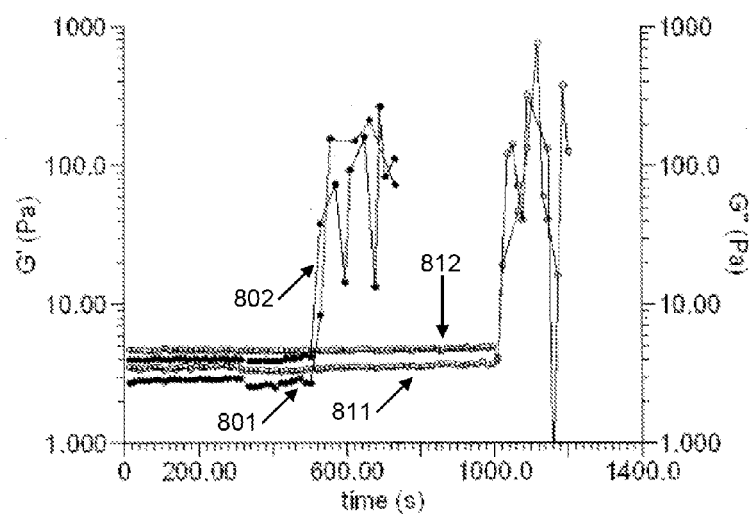

Turning now to FIG. 8, measures of the viscoelasticity of pure amorphous CPP gels in an oscillatory time sweep test are illustrated which reveal the setting times of pure amorphous CPP gels after injection at 25° C. (plots 811 and 812) and 37° C. (plots 801 and 802). A solvent trap was loaded in order to prevent evaporation and to ensure that rheological measurement was performed under stable conditions. The solvent trap was released after 300 seconds. A non-destructive oscillatory stress determined by a previous oscillatory stress test was loaded. A sharp increase of both G' (plots 801 and 811) and G" (plots 802 and 812) indicates the gelation and solidification of CPP gel after a short period of exposure to air. Increasing the temperature accelerates the setting of CPP gel, which is linked to water evaporation. The setting time at 25° C. was about 700 seconds after release of the solvent trap and about 200 seconds at 37° C.

The setting time or gelation time of injectable bone cement is critical to fill defects in and attach to native bone and provide mechanical support in a short time. Based on a classical sol-gel process, colloidal particles interact with each other to become a 3D network structure following water evaporation. The fast dissolution rate of amorphous CPP gel in aqueous solution caused by disentanglement of polyphosphate chains exposes abundant binding sites for exchangeable metal ions ($Ca^{2+}$, $Sr^{2+}$, $Mg^{2+}$, etc.) It also results in active interactions between CPP colloidal particles, accelerating the gelation process. To determine the setting point or critical gelation point of injectable CPP gel is crucial for the clinical application as injectable bone-healing materials.

Figure 9:
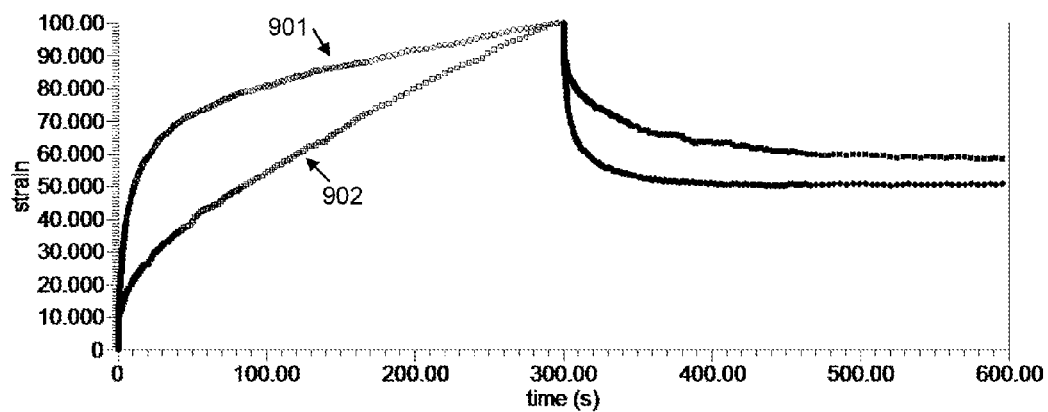
FIG. 9 is a graphical representation of a creep-recovery test on CPP gel samples in accordance with another example of the present invention.

The results of a creep recovery test for pure amorphous CPP (plot 901) and amorphous/crystalline composite CPP gels (plot 902) are illustrated in FIG. 9. In these tests a specimen is subjected to a creep test under a predetermined non-destructive oscillatory stress. Recovery is tested after releasing the stress for the same amount of time as in the creep test. Strain (%) has been recorded and normalized to distinguish the differences between pure amorphous CPP and amorphous/crystalline composite gels.

As seen in FIG. 9, pure amorphous CPP colloid subjected to a non-destructive oscillatory stress showed a creep response typical of structured fluids (901): an immediate elastic response, followed by a delayed elastic response, and eventually a viscous flow response. By releasing the uploaded oscillatory stress, an obvious recovery curve can be observed presumably due to the re-entanglement of temporally broken-up polyphosphate chains. The original network structure is restored to an integrity of about 50%.

By incorporation of crystalline CPP particles (FIG. 9, 902), the delayed elastic response is prolonged, indicating that filling particles further interact with unfolded polyphosphate chains in the CPP structured fluid, enhancing the bonding of the network. The original network structure is restored to an integrity of about 40%.

Figure 10:
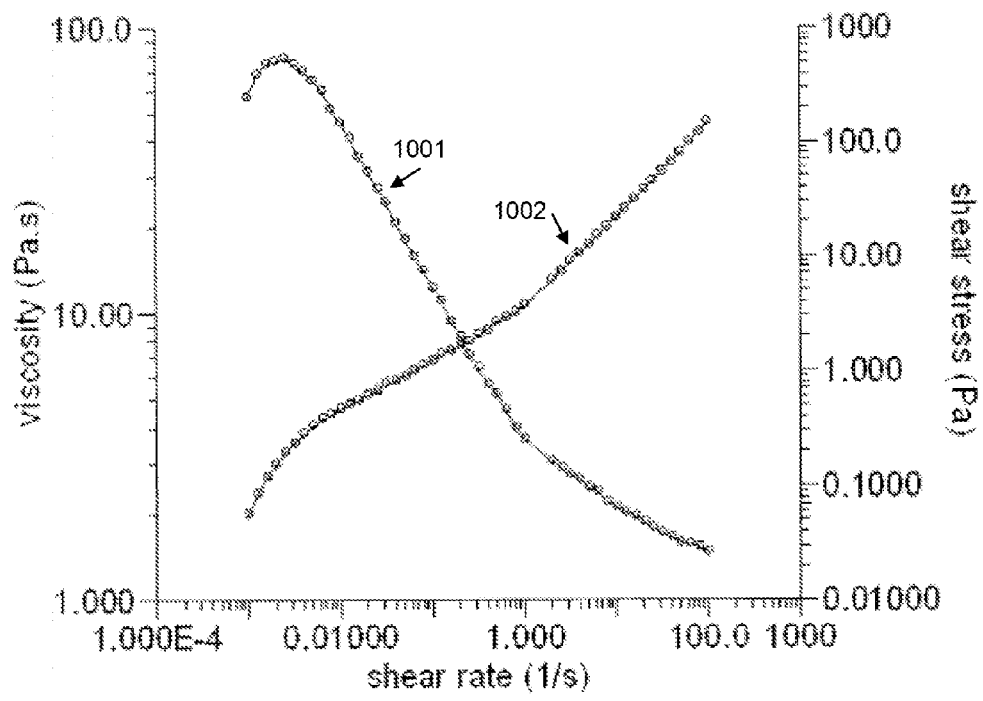
FIG. 10 is a graphical representation of a steady-state flow test on a pure CPP colloid sample in accordance with another example of the present invention.
Figure 12A:
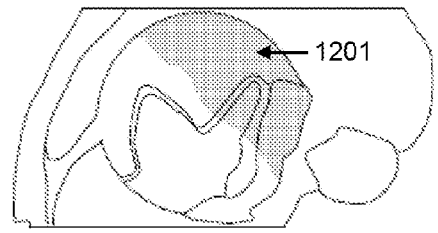
Figure 12B:
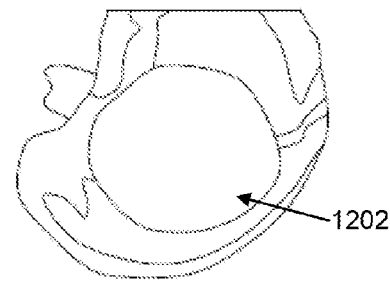

Turning now to FIG. 10, a graph shows a typical result of a steady state flow test performed within a shear rate range from 0.0001 to 100 per second to reveal the pseudoplastic property of a pure amorphous CPP colloid. Viscosity is indicated by plot 1001 and shear stress is indicated by plot 1002. The steady state flow measurement shows a typical shear thinning behavior with a first Newtonian plateau, a Power's law region, and a second Newtonian plateau, which is different from conventional ceramics suspension with constant viscosity during static shearing. In the first Newtonian region, the disentanglement of polyphosphate chain follows the increase of shear rate. In the Power's law region, disentanglement continues further, and the network structure starts to break at the bonding sites along polyphosphate chains, which causes a gradual decrease of viscosity. Until reaching the second Newtonian region, the disentanglement of polyphosphate chains and destruction of network structure diminishes, which results in another flattened region of constant viscosity, independent of the shear rate change. This measurement reveals a pseudo-plastic behavior of a pure amorphous CPP colloid which is very similar to most water-soluble polymers.

Turning now to FIG. 11-12, micro computed tomography (CT) data shows a rat femur defect 1101 (FIG. 11A) following the ex vivo injection of 20 ml pure amorphous CPP gel 1102. CT images were taken right after injection and 4 hours after injection. Three-dimensional (3D) images were reconstructed for the immediate injection (FIG. 11B) and 4 hours after injection (FIG. 11C). A representative section in Z-stack (FIG. 11D) is displayed to show the adhesion of CPP pure amorphous gel to bone tissue. Analogous images for amorphous/crystalline composite gels 1202 in rat femur defect 1201 are shown in FIG. 12A-D.

Figure 11A:
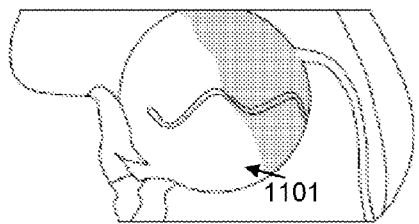
FIGS. 11A-11D and 12A-12D are micro-computed tomography scans of CPP gels injected into a defect in rat femur in accordance with another example of the present invention.
Figure 11B:
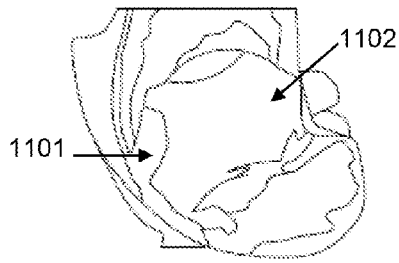
Figure 11C:
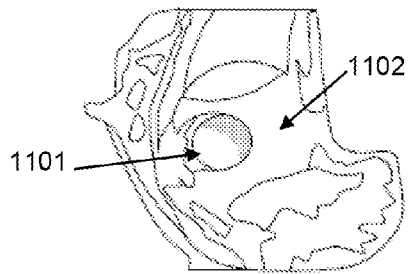
Figure 12C:
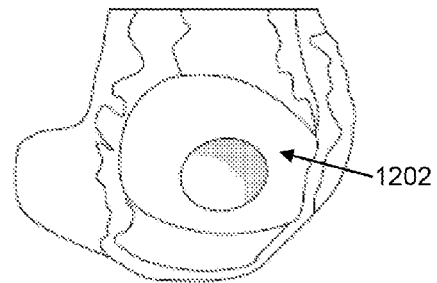
Figure 11D:
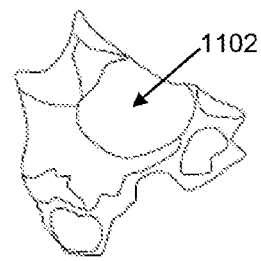
Figure 12D:
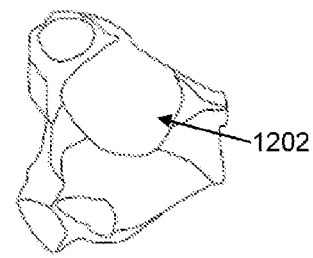

The reconstructed 3D image indicates that certain shrinkages are observed from the bone defects with the injection of both pure amorphous CPP and CPP amorphous/crystalline composite gels (FIG. 11C and FIG. 12C.) However, CPP complex gel shows less shrinkage than pure amorphous CPP gel, which is in part due to the incorporation of the crystalline CPP fillers. Both injected pure amorphous CPP and complex gel firmly attach to the bone defect wall, as shown in the images from Z direction (FIG. 11D and FIG. 12D.) CPP gel therefore can function as a fast-setting, injectable bone-healing material. CPP gel can be used in weight-bearing or non-weight-bearing applications.

After setting, the composite may convert to another compound. For instance, after about 1 hour to about 8 weeks after injection and setting, the composite may gradually convert to dicalcium phosphate anhydrate (DCPA) or dicalcium phosphate dihydrate (DCPD).

Figure 13:
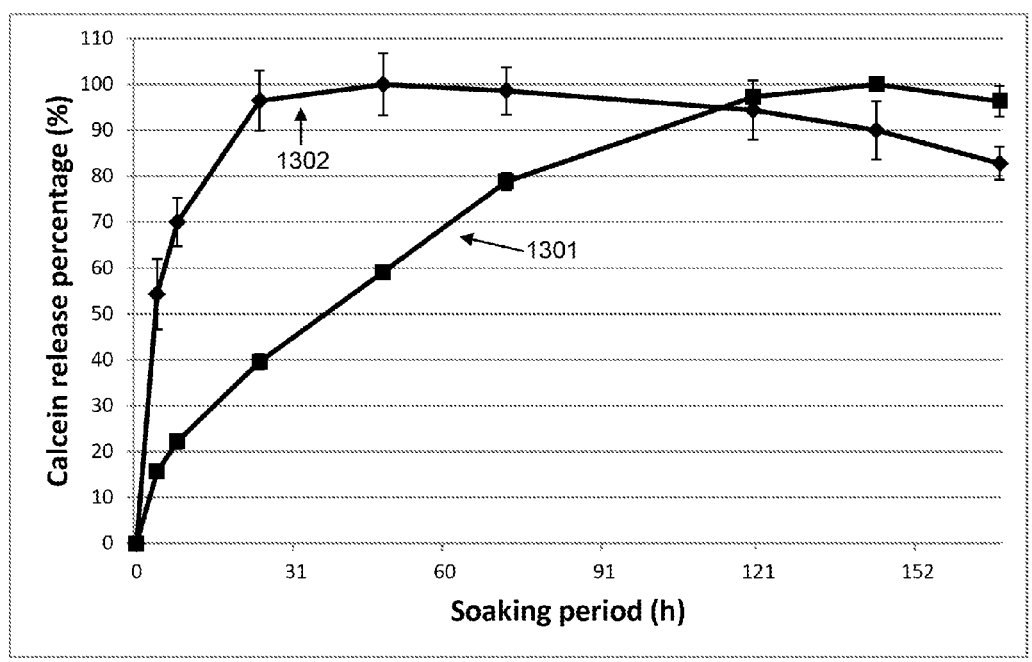
FIG. 13 is a graphical representation of the amount of calcein released from CPP gel samples following soaking steps of various lengths in accordance with another example of the present invention.

FIG. 13 shows the calcein release pattern from pure amorphous CPP gel (plot 1302) and crystalline:amorphous composite (plot 1301) CPP gel. The design of bone healing materials with multiple functionalities (including but not limited to bactericidal activity, drug loading capability, delivery of cells to the wound) has many possible uses. However, controlling drug release from implants in a sustainable manner has presented a challenge. In the present invention, drug molecules can be assembled into the CPP gel network by physical interactions during colloidal formation and gelation. One example of small molecule release in illustrated in FIG. 13. To mimic the behavior of antibiotics with smaller molecular weight (<1000), calcein, a water soluble fluorescent dye with green-yellow color, was dissolved in the solution for pure and composite (1:2) CPP colloid preparation. Calcein is known to chelate free calcium ions ($Ca^{2+}$) and has a maximum absorbance at wavelength of 560 nm. The increase of OD at 560 nm indicated the higher content of $Ca^{2+}$ bound with calcein has been released from CPP gel into solution. Thus, the quantification of calcein release suggests a release pattern for other drug molecules of small molecular weight.

Cylindrical gel specimens with calcein incorporated were prepared by the method described above and were placed into distilled H2O. The supernatant was serially measured until the OD reached a plateau. Calcein release from pure amorphous CPP gel is complete after about 30 hours. However, in the case of the composite release is more gradual and extends to about 150 hours, displaying a zero-order release pattern through the initial 120 hours. The surface of CPP microcrystal fillers in an amorphous CPP network might provide binding sites for calcein and therefore be largely responsible for extending the release of calcein. Composite CPP gel, then, possesses a drug-loading capability can be tuned by modifying the preparation parameters (including but not limited to ratio of amorphous to crystalline powder, pore size, pore network, and so forth.)

The calcein-release experiments provide a basis for use of materials generated by this process in clinical applications. These include but are not limited to orthopedic or dental healing or tissue repair; and tissue engineering of at least bone, muscle, cartilage, ligament, or tendon. Further, compositions of this kind can be used in controlling drug release. The drug could include genetic material such as DNAs or RNAs, a small molecule compound, or a protein. These gels can also be useful in cell therapy including microsphere or microcapsule applications, molecular imaging, treating inflammation, and cancer therapy.

As a person skilled in the art will readily appreciate, the above description is meant as an illustration of implementation of the principles of this invention. This description is not intended to limit the scope or application of this invention in that the invention is susceptible to modification, variation and change, without departing from the spirit of this invention, as defined in the following claims.

The invention claimed is:

1. A composition for bone or soft tissue repair, the composition comprising:
   a colloid, comprising amorphous calcium polyphosphate having a predetermined particle size mixed in an excess of aqueous fluid such that the colloid is injectable.

2. The composition according to claim 1, wherein the colloid is water soluble and viscoelastic.

3. The composition according to claim 1, wherein the amorphous calcium polyphosphate has a degree of polymerization of about 100.

4. The composition according to claim 1, wherein the composition undergoes gelation after injection, and solidifies after about sixty minutes.

5. The composition according to claim 1, further comprising a drug to be released after injection of the composition.

6. The composition according to claim 5, wherein the drug is substantially fully released for at least 30 hours after injection.

7. The composition according to claim 1, further comprising at least one of a metal, an organic compound, a polymer, and an inorganic ceramic material.

8. A composition for bone or soft tissue repair, the composition comprising:
   a colloid comprising amorphous calcium polyphosphate having a predetermined particle size and a quantity of crystalline calcium polyphosphate mixed in an aqueous fluid to form a composite colloid, the colloid being injectable.

9. The composition according to claim 8 having a ratio of amorphous calcium polyphosphate to crystalline calcium polyphosphate between about 1:1 to about 10:1.

10. The composition according to claim 9, wherein the ratio of amorphous calcium polyphosphate to crystalline calcium polyphosphate is about 2:1.

11. The composition according to claim 8, wherein composite colloid comprises crystals of calcium polyphosphate dispersed therein.

12. The composition according to claim 8, wherein the composite colloid sets to a solid within about 200 seconds when dried at about 37 degrees Celsius.

13. The composition according to claim 8, further comprising at least one of a metal, an organic compound, a polymer, and an inorganic ceramic material.

14. The composition according to claim 8, further comprising a drug to be released after injection of the composition, the drug being substantially fully released for at least 150 hours after injection.

15. A composition for bone or soft tissue repair, the composition comprising:
   a colloid comprising amorphous calcium polyphosphate having a predetermined particle size mixed in an excess of aqueous fluid such that the colloid is injectable, the amorphous calcium polyphosphate being produced by calcining monobasic calcium phosphate.

16. The composition of claim 15, wherein the monobasic calcium phosphate is calcined for about 4 hours to about 72 hours at a temperature of about 300 degrees Celsius to about 700 degrees Celsius.

17. The composition of claim 15, wherein the colloid is water soluble.

18. The composition of claim 15, wherein the amorphous calcium polyphosphate has a degree of polymerization of about 100.

19. The composition of claim 1, wherein a ratio of aqueous fluid to amorphous calcium polyphosphate is about 2:1 to about 100:1.

20. The composition of claim 15, wherein a ratio of aqueous fluid to amorphous calcium polyphosphate is about 2:1 to about 100:1.

* * * * *